United States Patent
Kojo

(10) Patent No.: US 11,490,796 B2
(45) Date of Patent: Nov. 8, 2022

(54) INSERTION ASSIST SYSTEM

(71) Applicant: OLYMPUS CORPORATION, Tokyo (JP)

(72) Inventor: Hiroyuki Kojo, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 289 days.

(21) Appl. No.: 16/847,870

(22) Filed: Apr. 14, 2020

(65) Prior Publication Data
US 2020/0237190 A1    Jul. 30, 2020

Related U.S. Application Data

(63) Continuation of application No. PCT/JP2017/037660, filed on Oct. 18, 2017.

(51) Int. Cl.
| | | |
|---|---|---|
| A61B 1/005 | (2006.01) | |
| A61B 1/00 | (2006.01) | |
| A61B 1/01 | (2006.01) | |
| A61B 1/233 | (2006.01) | |

(Continued)

(52) U.S. Cl.
CPC ........ *A61B 1/0055* (2013.01); *A61B 1/00071* (2013.01); *A61B 1/01* (2013.01); *A61B 1/233* (2013.01); *A61B 1/042* (2013.01); *A61B 1/07* (2013.01)

(58) Field of Classification Search
CPC ..... A61B 1/0055; A61B 1/00071; A61B 1/01; A61B 1/00098; A61B 1/00154
See application file for complete search history.

(56) References Cited

U.S. PATENT DOCUMENTS 3,915,157 A * 10/1975 Mitsui ............... A61B 1/00098
    600/107
4,407,273 A * 10/1983 Ouchi ............... A61B 1/00098
    600/107

(Continued)

FOREIGN PATENT DOCUMENTS

| JP | S52-71290 U | 5/1977 |
| JP | H06-261857 A | 9/1994 |

(Continued)

OTHER PUBLICATIONS

Japanese Office Action dated Oct. 12, 2021 received in 2019-549042.

(Continued)

*Primary Examiner* — Aaron B Fairchild
(74) *Attorney, Agent, or Firm* — Scully, Scott, Murphy & Presser, P.C.

(57) ABSTRACT

An insertion assist system includes a guide member and a shift member. The guide member brings an outside bend of a peripheral surface of an insertion body into contact with a guide surface of the guide member. The shift member shifts a direction of the distal end of the insertion body. The shift member comes into contact with an inside bend of the peripheral surface of the insertion body when the insertion body is bent. The shift member bends the insertion body toward the guide surface about the guide surface as a fulcrum when the shift member comes into contact with the inside bend and bends the insertion body.

15 Claims, 13 Drawing Sheets

(51) Int. Cl.
    *A61B 1/04*          (2006.01)
    *A61B 1/07*          (2006.01)

(56) References Cited

U.S. PATENT DOCUMENTS

| | | | |
|---|---|---|---|
| 4,436,087 A * | 3/1984 | Ouchi | A61B 1/12 600/153 |
| 5,562,602 A * | 10/1996 | Yabe | A61B 1/05 600/125 |
| 2013/0072958 A1 | 3/2013 | Ressemann et al. | |

FOREIGN PATENT DOCUMENTS

| | | |
|---|---|---|
| JP | 2002-558 A | 1/2002 |
| JP | 2002-17655 A | 1/2002 |
| JP | 2002-253484 A | 9/2002 |

OTHER PUBLICATIONS

Chinese Office Action dated Nov. 16, 2021 received in 201780094965.3.
Japanese Office Action dated Apr. 20, 2021 received in 2019-549042.
International Search Report dated Jan. 9, 2018 issued in PCT/JP2017/037660.
English translation of International Preliminary Report on Patentability together with the Written Opinion from related International Application No. PCT/JP2017/037660 dated Apr. 21, 2020.

* cited by examiner

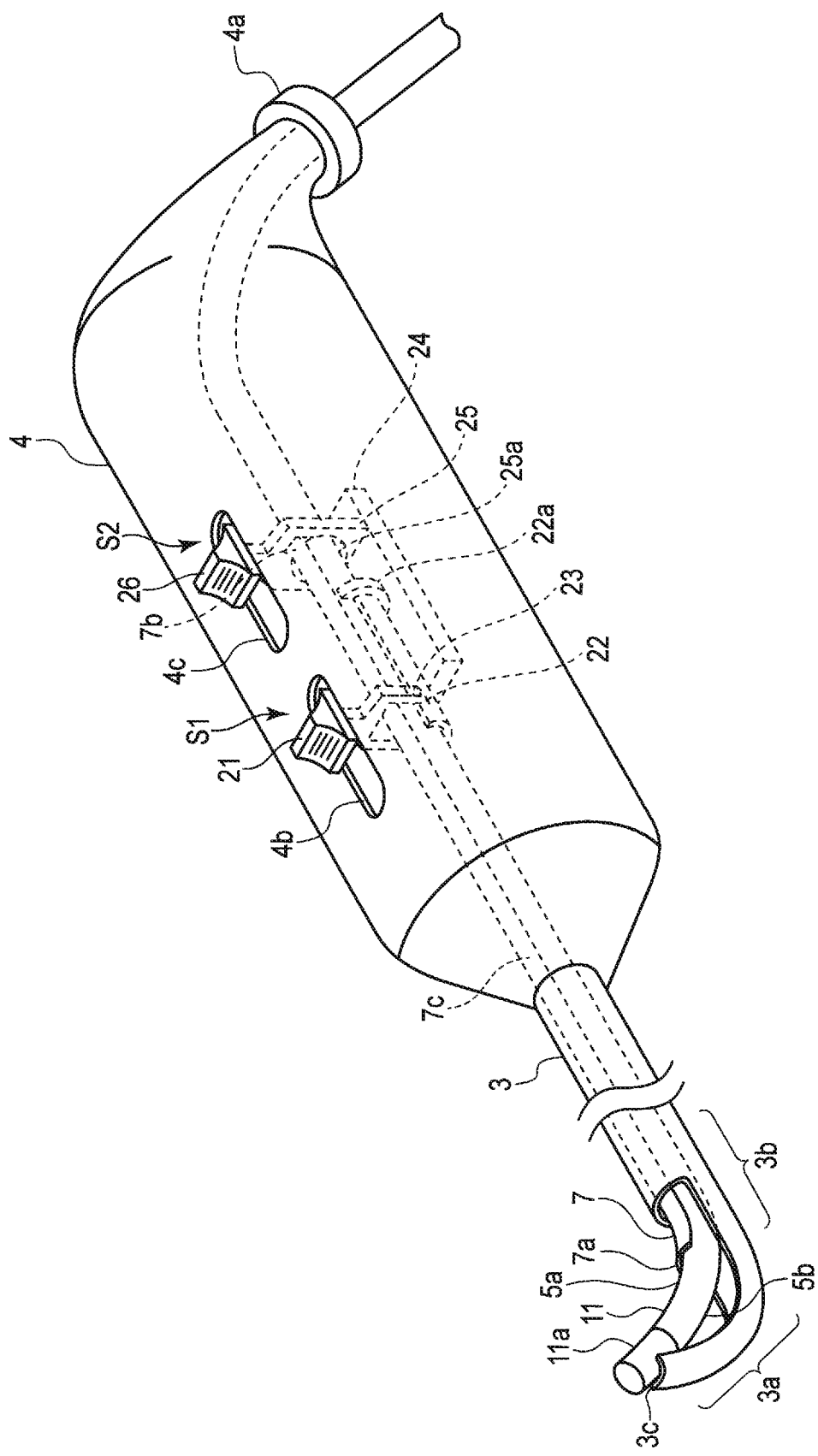
F I G. 4A

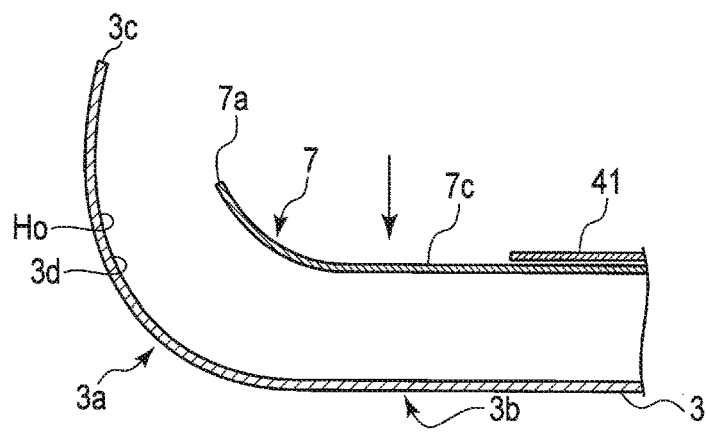
F I G. 11A
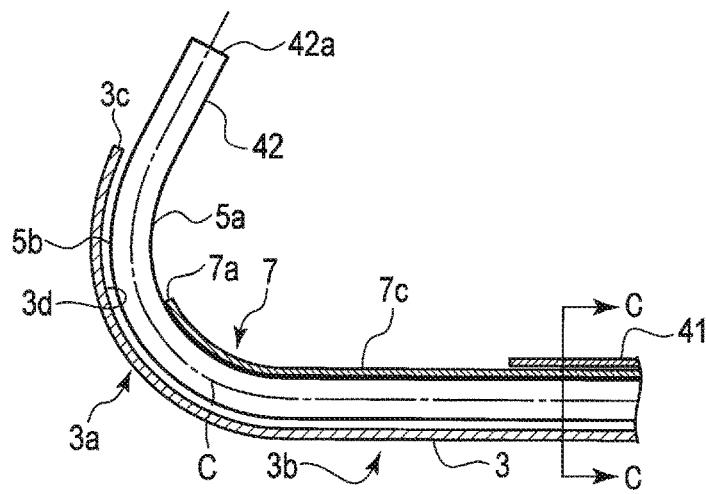
F I G. 11B
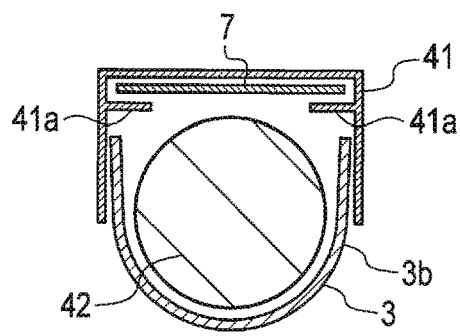
F I G. 11C

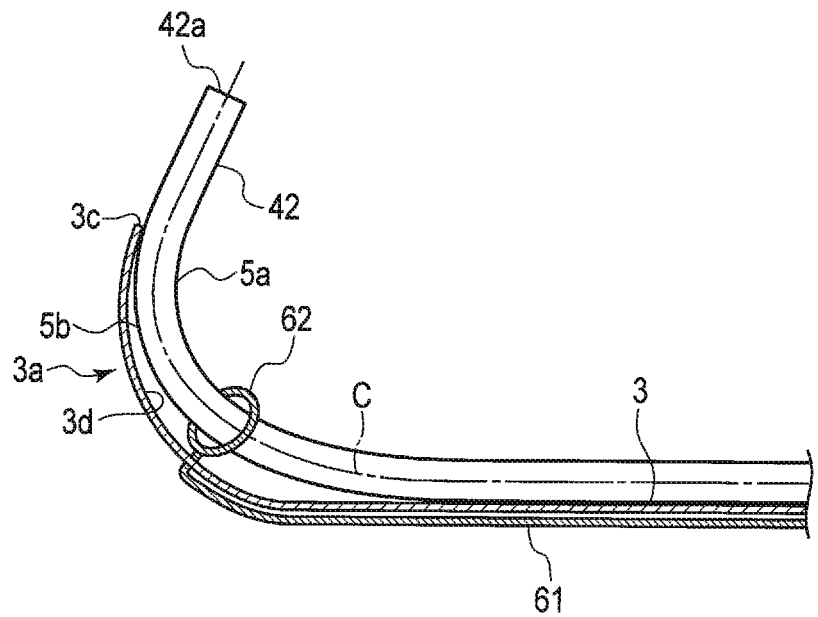
F I G. 14A
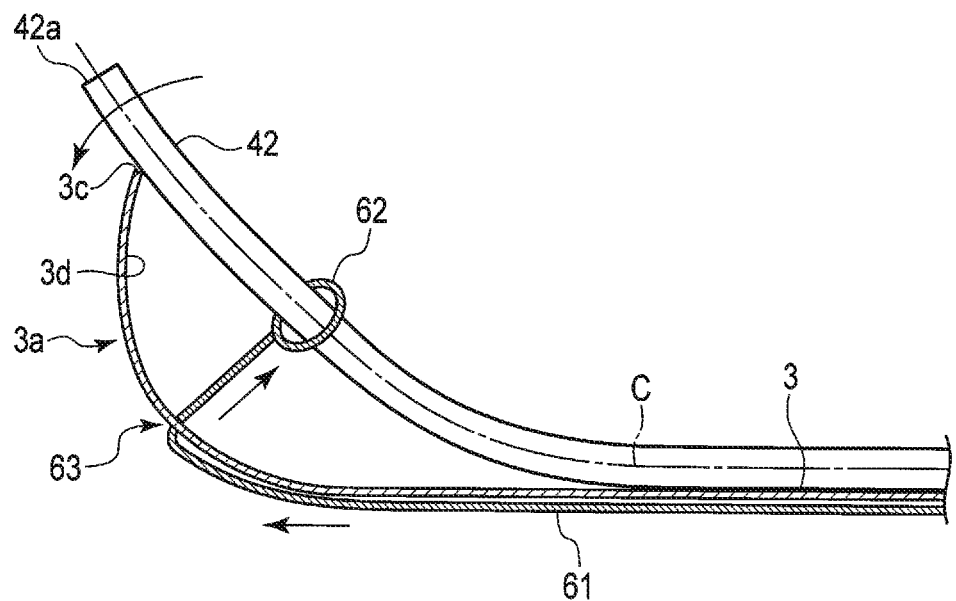
F I G. 14B

INSERTION ASSIST SYSTEM

CROSS-REFERENCE TO RELATED APPLICATIONS

This application is a Continuation Application of PCT Application No. PCT/JP2017/037660, filed Oct. 18, 2017, the entire contents of which are incorporated herein by reference.

BACKGROUND OF THE INVENTION

1. Field of the Invention

The present invention relates to an insertion assist system for assisting insertion of a flexible insert into a lumen and adjusting an angle of a distal end portion of the insert in the lumen.

2. Description of the Related Art

For example, when the inside of a maxillary sinus of a paranasal sinus is observed using a flexible endoscope, which is one of the flexible inserts, the distal end portion of the endoscope is inserted from the mouth of the nasal cavity, passed through the opening in the nasal cavity, and reaches the maxillary sinus. To observe such a paranasal sinus, various guide devices and methods have been proposed, since there are bending portions in the course of insertion. For example, U.S. Patent Application Publication No. 2013/072958A1 discloses a technique of guiding an insertion tip in a state in which a sleeve portion serving as a guide member is bent at a discretionary angle by a hand of an operator in order to allow a catheter serving as a flexible insert to reach a treatment site.

BRIEF SUMMARY OF THE INVENTION

According to one aspect of the present invention, an insertion assist system includes a guide member and a shift member. The guide member includes a guide surface configured to guide insertion of an insertion body. The guide member brings an outside bend of a peripheral surface of the insertion body into contact with the guide surface when the insertion body is bent toward the guide surface. The shift member is configured to shift a direction of a distal end of the insertion body. The shift member comes into contact with an inside bend of the peripheral surface of the insertion body, as a point of force, opposite to the outside bend of the peripheral surface across a center axis of the insertion body, at a position closer to a proximal end side of the insertion body than a position of the guide surface where the outside bend of the peripheral surface of the insertion body is capable of coming into contact when the insertion body is bent. The shift member bends the insertion body toward the guide surface about the guide surface as a fulcrum when the shift member comes into contact with the inside bend and bends the insertion body.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4A is a diagram conceptually showing a configuration of an operation portion of the insertion assist system.

FIG. 11A is a diagram showing a configuration example of a distal end portion of an insertion assist system according to a second embodiment.

FIG. 11B is a diagram showing a state of the distal end portion of the insertion assist system according to the second embodiment.

FIG. 11C is a cross-sectional view showing a cross-sectional configuration of the distal end portion of the insertion assist system according to the second embodiment.

FIG. 14A is a diagram showing a configuration example of a distal end portion of an insertion assist system according to a fifth embodiment.

FIG. 14B is a diagram showing a state of the distal end portion of the insertion assist system according to the fifth embodiment.

DETAILED DESCRIPTION

Hereinafter, embodiments will be described in detail with reference to the drawings.

First Embodiment

An insertion assist system 2 according to the first embodiment will be described.

The object to be assisted by the insertion assist system 2 is a long and flexible insert, and includes at least a flexible endoscope, a catheter, a guide wire, and the like, which are inserted into a body cavity or a lumen. That is, it is preferable that the object to be assisted by the insertion assist system 2 be a device that does not have a bending mechanism that actively bends at the distal end portion on the insertion side.

The object to be assisted is preferably a device on which, when the device is bent, a resilience (elastic force) or a restoring force to return from the bent state to a nearly linear state is exerted. The resilience in the present embodiment means a property which causes the material to be easily deformed appropriately when a force is applied, and has a high resilience from the deformation. In addition, the object to be assisted can be easily applied not only to a medical device or an observation device for a living body, but also to a long observation device which is inserted into an internal mechanism of a device, such as a pipe structure or an engine made of a rigid member, and has an imaging unit or the like or an observation window at its distal end, and also to a long member, such as a wire.

A flexible endoscope 1 assisted by the insertion assist system 2 of the present embodiment has a resilience or restoring force as described above. The flexible endoscope 1 also includes a paranasal sinus endoscope to observe a paranasal sinus described later.

Figure 1:
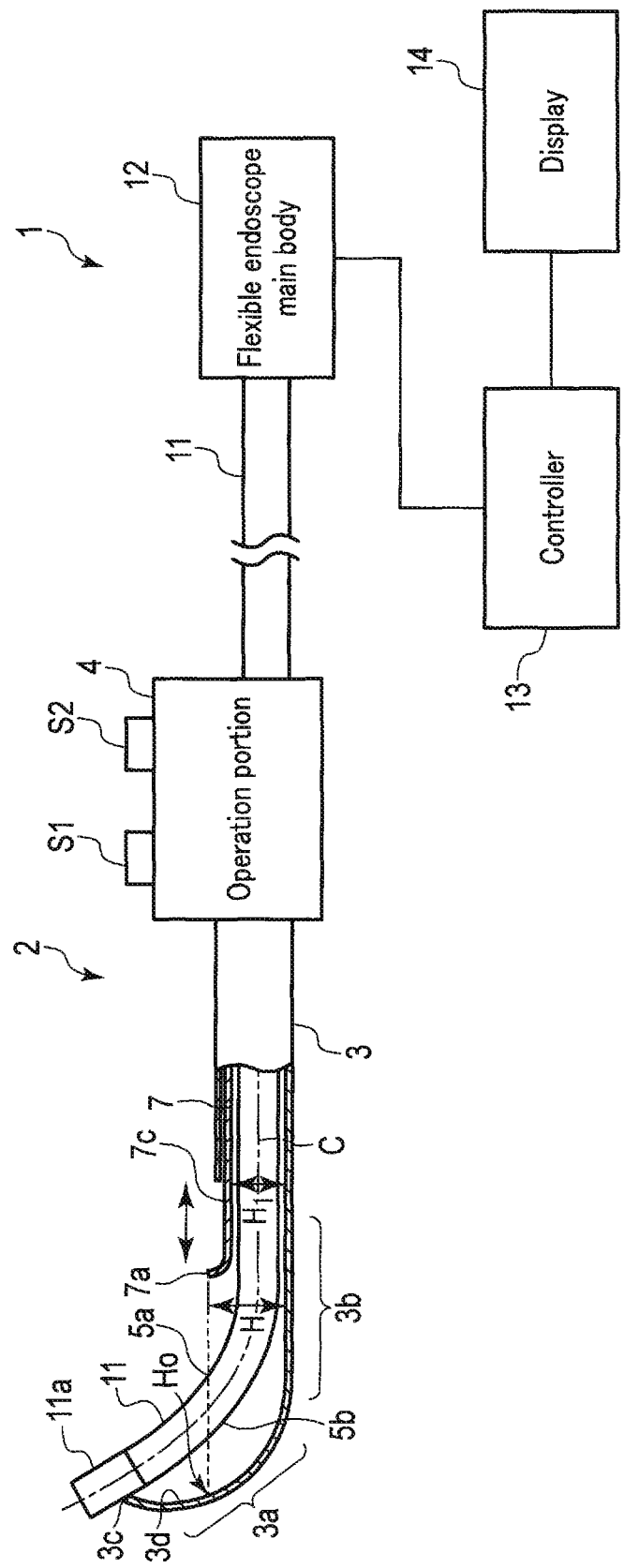
FIG. 1 is a diagram showing a conceptual configuration in which an insertion assist system according to a first embodiment is applied to a flexible endoscope.
Figure 2A:
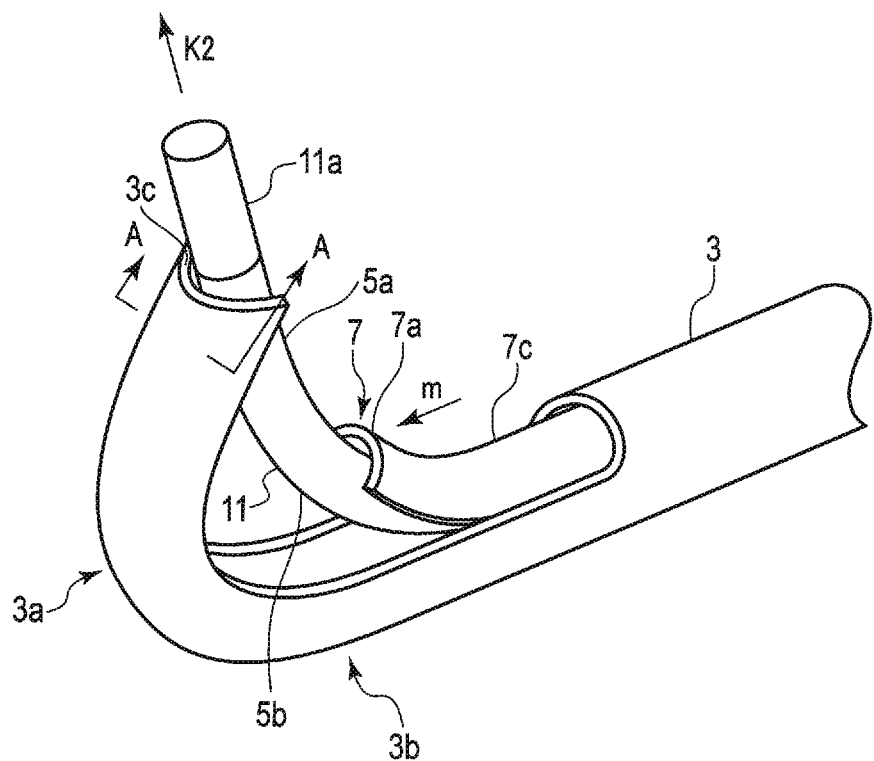
FIG. 2A is a diagram showing a state of angle adjustment of a flexible insertion body by the insertion assist system.
Figure 2B:
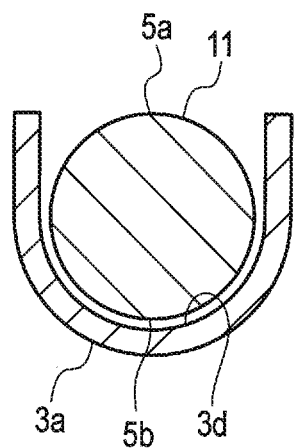
FIG. 2B is a cross-sectional view showing a cross-sectional shape of the insertion assist system taken along line A-A in FIG. 2A.
Figure 3A:
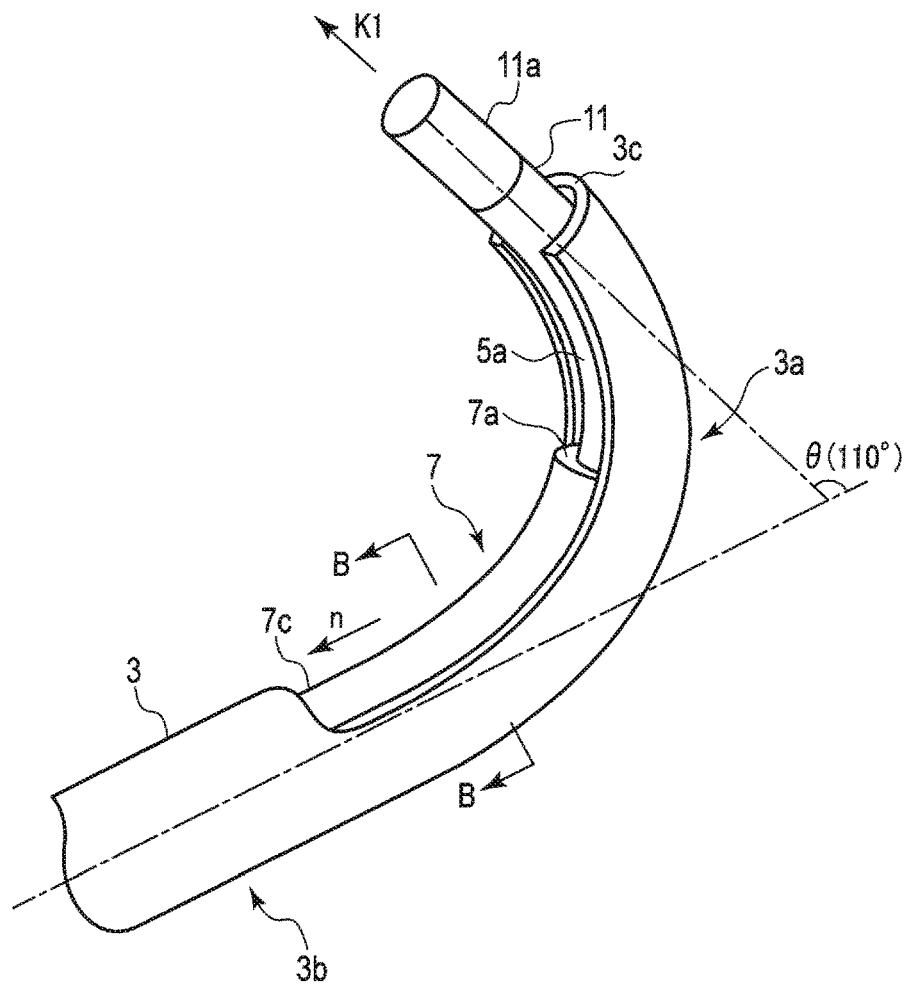
FIG. 3A is a diagram showing another state of angle adjustment of the flexible insertion body by the insertion assist system.
Figure 3B:
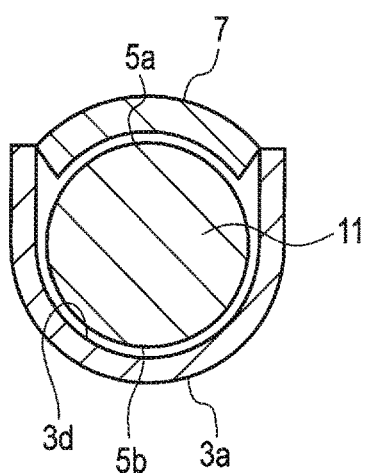
FIG. 3B is a cross-sectional view showing a cross-sectional shape of the insertion assist system taken along line B-B in FIG. 3A.

FIG. 1 is a diagram showing a conceptual configuration in which the insertion assist system 2 according to the first embodiment is applied to the known flexible endoscope 1. FIG. 2A and FIG. 3A are diagrams each showing an example of angle adjustment for a flexible insertion body by the insertion assist system 2. FIG. 2B is a cross-sectional view showing a cross-sectional shape of the insertion assist system 2 taken along line A-A in FIG. 2A. FIG. 3B is a cross-sectional view showing a cross-sectional shape of the insertion assist system 2 taken along line B-B in FIG. 3A.

As shown in FIG. 1, the flexible endoscope 1 includes a flexible insertion body 11 and a flexible endoscope main body 12 integrally connected to the insertion body 11. The flexible endoscope 1 having a known configuration can be used. The flexible endoscope main body 12 is connected to a controller 13 to perform control including image processing and a display 14 to display image information including a captured observation image.

A distal end portion 11a of the insertion body 11 includes an illumination window to at least irradiate illumination light, an observation window to optically capture a light image serving as an observation image, and the like. Since the distal end portion 11a [rigid portion] has a structure in which the windows are arranged, cylindrical tube member formed of a rigid material, for example, a metal material, is used as an exterior member of the distal end portion. Although not shown, at least a light guide to guide illumination light and an optical fiber to transmit a captured light image are provided to pass through the insertion body 11.

An imaging unit (not shown) including an imaging element, such as a CCD or a CMOS, is provided in the flexible endoscope main body 12. The imaging unit forms a captured light image received through a light receiving optical fiber, converts the image into a video signal by photoelectric conversion, and sends the video signal to the controller 13. The controller 13 performs various image processing on the video signal, and causes the display 14 to display an image captured by the imaging unit.

The insertion assist system 2 of the present embodiment includes a fixed guide 3 [guide member] through which the insertion body 11 of the flexible endoscope 1 as a flexible insert is inserted, an operation portion 4 configured to be pushed in and pulled out from the insertion body 11 by a discretionary amount (a discretionary distance in a longitudinal direction of the insertion body 11), and a movable guide 7 [shift member or change member] configured to slide in the longitudinal direction (m or n) so that the insertion body 11 abuts on an angle adjustment portion 3a which bends on the distal end side of the fixed guide 3. The movable guide 7 [shift member] is configured to move forward and backward with respect to the fixed guide 3 [guide member]. That is, the movable guide 7 [shift member] is relatively movable with respect to the fixed guide 3 [guide member]. In the following description, an abutting surface (both side surfaces and the bottom surface of a U shape) of the one-way bendable groove portion of the fixed guide 3 in which the insertion body 11 is accommodated and directed is referred to as a guide surface 3d. The guide surface 3d guides the insertion of the insertion body 11 into the body cavity.

Here, in the fixed guide 3, with respect to the linear longitudinal axis direction of a linear portion 3b, a side on which the angle adjustment portion 3a is provided is referred to as a distal end side or a distal end direction, and a side connected to the operation portion 4 is referred to as a proximal end side or a proximal end direction of the fixed guide 3. Further, the direction toward the angle adjustment portion 3a or the distal end of the fixed guide 3 as viewed from the movable guide 7 is defined as the front (or the distal end side). In contrast, the direction toward the operation portion 4 as viewed from the movable guide 7 is defined as the rear (or the proximal end side). In the angle adjustment portion 3a, the bending inner surface is referred to as the guide surface 3d, and its end is referred to as a distal end 3c. The insertion body 11 protruding from the distal end 3c of the guide surface 3d (to be described later) projects in a direction intersecting with a linear longitudinal axis direction of a cylindrical tube according to the bending direction of the angle adjustment portion 3a.

As described later, the insertion body 11 is moved forward by moving the movable guide 7 in the longitudinal axis direction toward the angle adjustment portion 3a of the fixed guide 3, so that an inside bend 5a at the peripheral surface of the insertion body 11 comes into contact with the movable guide 7. The insertion body 11 is pushed toward the guide surface 3d of the angle adjustment portion 3a and is bent. An outside bend 5b at the peripheral surface of the insertion body 11 can come into contact with the guide surface 3d.

The outside bend 5b refers to a region of the peripheral surface of the insertion body 11 that faces or contacts the guide surface 3d when the insertion body 11 is bent. The outside bend 5b refers to a region of the peripheral surface of the insertion body 11 opposite to the inside bend 5a with respect to a center axis C of the insertion body 11. With this bending, the distal end portion 11a of the insertion body 11 is directed obliquely rearward and upward with respect to the fixed guide 3. On the other hand, when the movable guide 7 is moved rearward with respect to the fixed guide 3, the outside bend 5b of the insertion body 11 is separated from the guide surface 3d due to the resilience of the insertion body 11, and tends to return from the bending state to the linear state. As a result, the outside bend 5b is directed obliquely upward in the forward direction with respect to the fixed guide 3. Thus, the direction of the distal end portion 11a of the insertion body 11 can be shifted depending on the position of the movable guide 7 with respect to the fixed guide 3.

The insertion body 11 of the flexible endoscope 1 is inserted from the proximal end side toward the distal end side of the fixed guide 3. At this time, the distal end portion 11a of the insertion body 11 moves from the proximal end side toward the distal end side while abutting along the guide surface 3d of the fixed guide 3. Since the insertion body 11 has resilience, the flexible portion following the distal end portion 11a is separated from the guide surface 3d and moves in a slightly raised state. The distal end portion 11a of the insertion body 11 can project from the distal end 3c of the guide surface 3d of the fixed guide 3. With regard to the present embodiment, an example in which the linear portion (for example, a straight tube) 3b is integrated with the proximal end side of the angle adjustment portion 3a will be described. However, a slight bending of the linear portion is allowed unless the insertion body 11 comes off from the fixed guide 3 at an exposed portion of the fixed guide 3.

The operation portion 4 includes a movement operation portion S1 [first operation portion] in which the flexible endoscope 1 is mounted to be inserted therethrough, so that the insertion body 11 is subjected to insertion movement and removal movement within the fixed guide 3. The operation portion 4 also includes a guide operation portion S2 [second operation portion] to slide the movable guide 7. Here, the insertion movement and the removal movement do not suggest that the flexible endoscope is inserted into and removed from the body of an observation subject person, but suggest that when an observation target is observed through the flexible endoscope 1 once inserted into a body cavity, a minimum amount of movement to shift the observation visual field direction and the observation position is performed with respect to the observation target.

The fixed guide 3 has a tubular shape such as a cylindrical tube made of a rigid member, such as a metal member or a rigid resin member, and linearly extends from the operation portion 4. As shown in FIG. 2A, the fixed guide 3 has a side surface which is partially cut off in the longitudinal direction on the distal end side. As shown in the cross-sectional view taken along line A-A in FIG. 2B, the cut-off distal end portion of the fixed guide 3 is in the form of a half pipe having a substantially U-shaped cross section in a direction orthogonal to the longitudinal direction of the fixed guide 3. The cut-off distal end portion includes both the linear portion 3b to move the movable guide 7 along the linear longitudinal axis and the angle adjustment portion (bending portion) 3a extending from the distal end of the linear portion 3b so as to bend in one direction. The angle adjustment portion 3a of the fixed guide 3 is not limited to a shape having a bend continued to the distal end (the position distal to the operation portion 4 along the guide surface 3d), but may be a shape having a linear portion near the distal end. This linear portion is also included in the angle adjustment portion 3a.

If the flexible endoscope 1 is inserted through an opening portion 35 reaching an observation target site or treatment target site in the subject, the bending angle (guide direction) of the angle adjustment portion 3a is set to an optimum angle (insertion direction) to pass the flexible endoscope through the opening portion 35. Further, the observation direction at the observation target site is also set to a desired direction.

As shown in FIG. 3A, an adjustment angle θ is defined by a central axis of the linear portion 3b of the fixed guide 3 and a direction K1 in which the distal end 3c of the angle adjustment portion 3a is directed. The adjustment angle θ may vary from case to case. For example, when treating the maxillary sinus of a paranasal sinus, the adjustment angle θ is preferably about 110°. Here, the adjustment angle is within a range of an angle indicated by a direction in which the distal end portion 11a faces when the insertion body 11 swings about the distal end 3c of the guide surface 3d of the angle adjustment portion 3a of the fixed guide 3 (direction K1 in FIG. 3a), that is, a range within which the insertion body swings in the observation direction and the insertion direction (hereinafter referred to as a bending angle). Of course, the bending angle of the bending portion can be set based on a desired adjustment angle depending on the application. Note that the guide surface 3d does not need to have a shape that is all bent in one direction, and may have a linear shape near the distal end 3c.

In the present embodiment, the cross section of the fixed guide 3 is shown as a cylinder and a U shape as an example. However, the cylinder shape may be other shapes, such as an ellipse and a rectangle, according to the cross section of the flexible insert. Further, the cross section of the guide surface 3d of the fixed guide 3 does not need to be U-shaped. For example, the cross section may be V-shaped or concave, as long as the fixed guide 3 has an opening portion through which the insertion body 11 (flexible insert) is inserted and removed and a groove portion that accommodates and directs the insertion body 11. In the cross section, the groove portion may or may not have a bottom, as long as the insertion body 11 does not fall off.

The movable guide 7 is movably fitted in the cylindrical tube of the fixed guide 3 as shown in FIG. 2B. The cross section of the movable guide 7 has an arc shape along the inner surface of the fixed guide 3. In the linear portion of the movable guide 7, the cross section may have a flat shape, not an arc shape. In this example, both ends of the movable guide 7 are located inside the U-shaped linear portion 3b of the fixed guide 3 in the cross-sectional view.

A guide distal end portion 7a of the movable guide 7 is warped from the distal end of an intermediate member 7c, which will be described later, toward the distal end along the bending shape of the guide surface 3d of the angle adjustment portion 3a. In other words, the guide distal end portion 7a is warped toward the distal end 3c of the angle adjustment portion 3a so as to be parallel to the guide surface 3d along the curvature of the guide surface 3d of the angle adjustment portion 3a.

In the present embodiment, the guide distal end portion 7a presses the peripheral surface (the inside bend 5a) of the insertion body 11 of the flexible endoscope 1 toward the angle adjustment portion 3a to bring the peripheral surface (the outside bend 5b) of the insertion body 11 of the flexible endoscope 1 close to the angle adjustment portion 3a. At this time, as shown in FIG. 1, the guide distal end portion 7a has a height H that matches the curvature of the angle adjustment portion 3a so that at least the insertion body 11 is not damaged or forcibly bent. Here, the height H is the distance from the guide distal end portion 7a to the surface of the linear portion 3b opposite to the guide distal end portion 7a across the insertion body 11. The height H is greater than a distance H1 from an intermediate portion 7c between the guide distal end portion 7a and a proximal end 7b (see FIG. 4A) of the movable guide 7 to the surface of the linear portion 3b opposite to the guide distal end portion 7a across the insertion body 11. Preferably, it is desired that the height H of the guide distal end portion 7a reach a height of a nearly central part Ho where the arc of the bend of the angle adjustment portion 3a becomes the deepest, and the peripheral surface of the insertion body 11 be brought into contact with the guide surface 3d of the angle adjustment portion 3a without an uplift from the guide surface 3d. Since the insertion body 11 has resilience, the peripheral surface of the insertion body 11 can be brought into contact with the angle adjustment portion 3a in the nearly central part Ho of the angle adjustment portion 3a regardless of the direction of gravity. As a result, the insertion body 11 is brought into contact with the angle adjustment portion 3a along the bending shape of the angle adjustment portion 3a, and the contact state is easily maintained. However, it is desirable but not essential that the height H of the guide distal end portion 7a reach the height of the nearly central part Ho of the angle adjustment portion 3a.

When the movable guide 7 moves to the distal end side of the fixed guide 3, the guide distal end portion 7a comes into contact with the side surface (the peripheral surface (the inside bend 5a)) of the insertion body 11 of the flexible endoscope 1. Thereafter, the guide distal end portion 7a pushes the insertion body 11 to bring the outside bend 5b on the opposite side of the inside bend 5a of the insertion body 11 closer to the guide surface 3d of the angle adjustment portion 3a. When the guide distal end portion 7a brings the outside bend 5b of the insertion body 11 into contact with the guide surface 3d of the angle adjustment portion 3a, the insertion body 11 of the flexible endoscope 1 is brought into contact with the angle adjustment portion 3a following the shape of the angle adjustment portion 3a. At this time, if the movable guide 7 is moved to the most distal end, the side surface (the outside bend 5b) of the insertion body 11 of the flexible endoscope 1 comes into contact with the guide surface 3d of the angle adjustment portion 3a. However, the movable guide is stopped before an overload or stress is applied to the insertion body 11.

Furthermore, the movable guide 7 may be formed into a plate shape from an elastically deformable material such as a resin material. When the angle of the insertion body 11 is adjusted by moving the movable guide 7, the tip of the guide distal end portion 7a elastically deforms to release the load, when the pressing on the peripheral surface of the insertion body 11 is overloaded. Thus, the movable guide 7 made of an elastically deformable material can prevent stress from being applied to the insertion body 11. When the elastically deformable movable guide 7 is accommodated in the cylindrical tube portion of the fixed guide 3, the width direction of the movable guide 7 is preferably elastically deformed so as to be bent along the inner peripheral surface of the cylindrical tube portion of the fixed guide 3. Further, the tip of the guide distal end portion 7a may be formed to be rigid so as not to enter the inside of the cylindrical tubular portion of the fixed guide 3. In this case, the guide distal end portion 7a comes into contact with and stops at the tip of the cylindrical tube of the fixed guide 3.

Referring to FIG. 2A and FIG. 3A, the angle adjustment in the observation direction of the insertion body 11 of the flexible endoscope 1 by the fixed guide 3 and the movable guide 7, and the angle adjustment in the protruding direction of the insertion body 11 passing through the opening portion 35 in the body cavity existing on the insertion path leading to the observation target will be described.

As shown in FIG. 2A, when the angle adjustment in the observation direction is performed in the insertion body 11 of the flexible endoscope 1 and when the insertion body 11 is passed through the opening portion 35 in the body cavity, the insertion body 11 is inserted through the operation portion 4 and the fixed guide 3, and the distal end portion 11a of the insertion body 11 is attached so as to project from the distal end 3c of the angle adjustment portion 3a. When the insertion assist system 2 in which the flexible endoscope 1 is mounted is inserted into an actual body cavity, the distal end portion 11a of the insertion body 11 is disposed at a position where the distal end portion 11a is aligned with the distal end of the angle adjustment portion 3a or at a slightly retracted position, so that the flexible endoscope 1 may not be detached from the U-shaped angle adjustment portion 3a. At this time, the resilience of the insertion body 11 acts in the direction in which the insertion body 11 extends linearly. Therefore, as shown in FIG. 2A, in the parts of the angle adjustment portion 3a excluding the distal end, the insertion body 11 is separated, that is, lifted from the guide surface 3d, and a direction K2 is 90 degrees or less with respect to the insertion direction (the longitudinal direction of the linear portion 3b of the fixed guide 3).

Next, the operator (observer) slides the movable guide 7 in the direction m toward the distal end side of the fixed guide 3, places the guide distal end portion 7a on the side surface (inside bend 5a) of the insertion body 11 as shown in FIG. 3A, and pushes the insertion body 11 in the direction toward the angle adjustment portion 3a without moving the insertion body 11 forward or backward. That is, the movable guide 7 can come into contact with the inside bend 5a of the peripheral surface of the insertion body 11, as a point of force, on the opposite side of the outside bend 5b across the central axis C of the insertion body 11 on the proximal end side of the position of the guide surface 3d with which the outside bend 5b of the peripheral surface of the insertion body 11 can come into contact. When the movable guide 7 is in contact with the inside bend 5a of the insertion body 11, the insertion body 11 can be bent toward the guide surface 3d about a fulcrum that is the guide surface 3d. In the present embodiment, the insertion body 11 is bent at a fulcrum that is the distal end 3c of the angle adjustment portion 3a with which the peripheral surface of the insertion body 11 is in contact, and the distal end portion 11a of the insertion body 11 is swung to be directed to the proximal end side of the fixed guide 3. By this swinging, the direction K2 (observation direction K2) of the insertion body 11 is swung up to the direction (observation direction K1) of the above-described angle θ (110 degrees) with respect to the insertion direction (longitudinal direction of the linear portion 3b of the fixed guide 3). The maximum angle θ of 110 degrees can be changed by changing the bending shape of the angle adjustment portion 3a when manufacturing the system.

Conversely, when the movable guide 7 is moved in the direction n toward the proximal end side of the fixed guide 3, the guide distal end portion 7a retracts, and the degree of pressing the guide distal end portion 7a to the peripheral surface (the inside bend 5a) of the insertion body 11 is reduced. Therefore, the resilience of the insertion body 11 acts in the direction in which the insertion body 11 extends linearly, and the peripheral surface (the outside bend 5b) of the insertion body 11 is separated from the guide surface 3d, as shown in FIG. 2A. Thus, the distal end portion 11a of the insertion body 11 swings about a fulcrum that is the distal end 3c of the angle adjustment portion 3a, and moves in the direction K2 toward the distal end. As described above, by moving the movable guide 7 so as to retract toward the proximal end side of the fixed guide 3, the bending state of the insertion body 11 can be changed. In this description, the direction toward the fixed guide 3 as viewed from the movable guide 7 is defined as the front (or the distal side), and the direction toward the operation portion 4 as viewed from the movable guide 7 is defined as the rear (or the proximal end side).

In the present embodiment, the bending state of the insertion body 11 is changed by moving the movable guide 7 forward and backward with respect to the fixed guide 3 in the longitudinal axis direction. That is, when the movable guide 7 is moved to the front of the fixed guide 3, the insertion body 11 is pushed toward the angle adjustment portion 3a and bent. Due to this bending, the insertion body 11 projecting obliquely upward and forward from the fixed guide 3 swings obliquely upward and backward about a fulcrum that is the distal end 3c of the fixed guide 3. Conversely, when the movable guide 7 is moved rearward, the bending of the insertion body 11 returns to a straight line due to the resilience. Therefore, the insertion body 11 projecting obliquely upward and backward from the fixed guide 3 swings obliquely upward and forward about a fulcrum that is the distal end 3c of the fixed guide 3. With these swings, the direction of the imaging window (observation direction) provided at the distal end portion 11a of the insertion body 11 can be shifted.

Figure 4B:
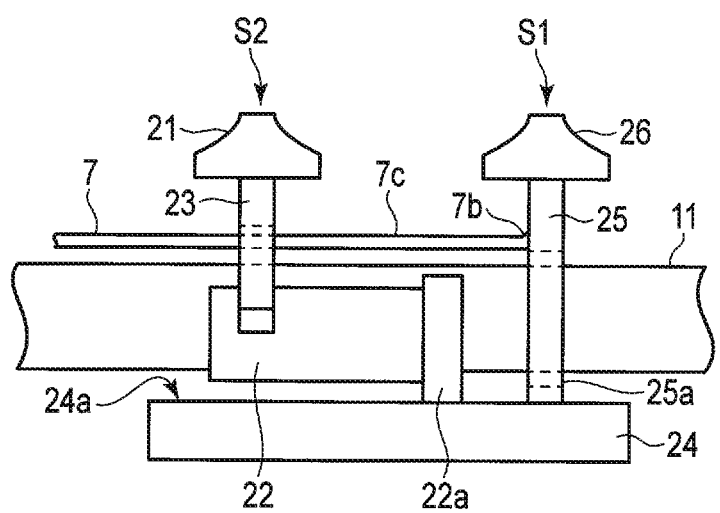
FIG. 4B is a diagram showing an example of a connection configuration between an insertion body and each operation element in a guide operation portion.

Next, with reference to FIG. 4A and FIG. 4B, a configuration example to move the movable guide 7 and inserting and removing the insertion body 11 in the operation portion 4 will be described. FIG. 4A is a diagram conceptually showing a configuration of the operation portion of the insertion assist system. FIG. 4B is a diagram showing an example of a connection configuration between the insertion body 11 and each of operation elements 21 and 26 in the guide operation portion S2.

In this example, the operation portion 4 includes a housing having a cylindrical shape. The front end side of the housing of the operation portion 4 is provided with the fixed guide 3, and the rear end side thereof is provided with an introduction port 4a to draw the insertion body 11 of the flexible endoscope 1 into the inside. The operation portion 4 further includes a movement operation portion S1 disposed on a side of the fixed guide 3, a guide operation portion S2 disposed on a side of the flexible endoscope main body 12, and a braking member 24.

When the movement operation portion S1 is moved along a sliding slit 4b, the insertion body 11 is moved to be inserted (projecting movement of projecting the distal end portion 11a of the insertion body 11 from the distal end 3c of the angle adjustment portion 3a) and to be removed. When the guide operation portion S2 is moved along a sliding slit 4c, the movable guide 7 is moved within the fixed guide 3.

The movement operation portion S1 will be described with reference to FIG. 4A and FIG. 4B.

The movement operation portion S1 includes a movement operation element 21, a semicylindrical gripping member 22, a stopper portion 22a provided on the rear end side of the gripping member 22, and a support member 23 to connect the gripping member 22 and the movement operation element 21.

The movement operation element 21 is integrally connected to the gripping member 22 by the support member 23 via the sliding slit 4b. The support member 23 is branched into two arms so that the movable guide 7 can pass between them, and the ends of the arms are fixed to the gripping member 22. The gripping member 22 and the support member 23 may be made of a resin material by integral molding.

The gripping member 22 has a semicylindrical shape with the outer periphery being partially cut-out, which allows passage of the movable guide 7. The gripping member 22 is attached and fixed to the insertion body 11. The flange-shaped stopper portion 22a is provided on the rear end side (a side of locking member 25) of the gripping member 22. The stopper portion 22a also has a partially cut-out C shape, which allows passage of the movable guide 7.

In the description of the present embodiment, an example in which the gripping member 22 is fixed so as to grip the insertion body 11 will be described. If the gripping member 22 is configured to be openable and closable and configured to grip and hold the insertion body 11 by the elastic force of the elastic member, it is possible to provide versatility so that the insertion body 11 having a different diameter can be gripped.

The outer diameter of the stopper portion 22a is set to a size that cannot pass through a through hole 25a opened in the locking member 25 described later. Note that the gripping member 22, the stopper portion 22a, and the support member 23 may be made of a resin material by integral molding. Alternatively, the gripping member 22, the stopper portion 22a, and the support member 23 may be separately manufactured, and may be integrally bonded with an adhesive.

As will be described later, the length of the gripping member 22 including the stopper portion 22a in the longitudinal axis direction corresponds to the distance by which the rigid distal end portion 11a of the insertion body 11 is pushed out distally so as not to abut against the movable guide 7 at the position of the angle adjustment portion 3a. In other words, when the guide operation portion S2 is moved toward the distal end of the fixed guide 3, the guide operation portion S2 comes into contact with the stopper portion 22a and thereafter pushes the gripping member 22 and integrally pushes out the insertion body 11 toward the distal end. That is, when the movable guide 7 approaches the distal end portion 11a of the insertion body 11, the movable guide 7 moves to the distal end side together with the insertion body 11 from the middle so as not to abut against the insertion body 11. When the distal end portion 11a of the insertion body 11 projects from the fixed guide 3, the movable guide 7 abuts against the insertion body 11.

Next, the guide operation portion S2 will be described.

The guide operation portion S2 includes a guide operation element 26 and a locking member 25. The locking member 25 has a plate shape, and has in an approximately central portion the through hole 25a which allows passage of the insertion body 11 as an insert. The locking member 25 is connected to the proximal end 7b of the movable guide 7. The through hole 25a has a diameter that allows passage of the insertion body 11, but does not allow passage of the stopper portion 22a. That is, the diameter of the through hole 25a is larger than the outer diameter of the insertion body 11 and smaller than the outer diameter of the stopper portion 22a. Further, the proximal end side of the movable guide 7 is fixed near the through hole 25a. The guide operation element 26 is integrally connected to the locking member 25 via the sliding slit 4c. When the guide operation element 26 is moved, the movable guide 7 moves forward and backward in the fixed guide 3.

The function of the operation by the operation portion 4 configured as described above will be described.

Figure 5:
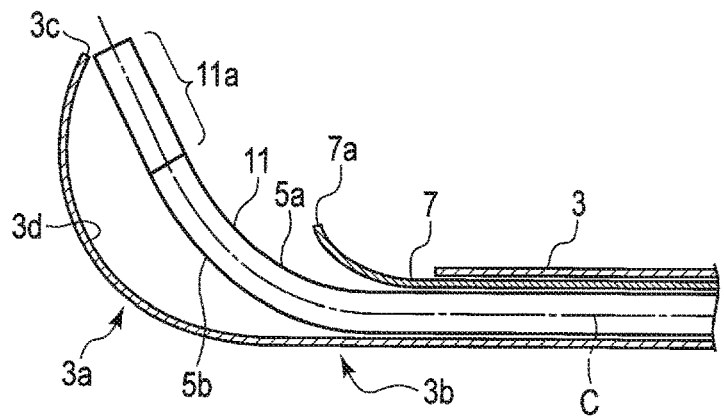
FIG. 5 is a diagram showing a state in which a movable guide at a distal end portion of the insertion assist system is retracted.

As shown in FIG. 5, when the insertion assist system 2 with the flexible endoscope 1 attached thereto is inserted into a body cavity, the distal end portion 11a of the insertion body 11 is disposed at a position where the distal end of the angle adjustment portion 3a comes into contact so that the flexible endoscope 1 does not come off the U-shaped angle adjustment portion 3a.

Here, a configuration in which the stopper portion 22a and the locking member 25 described above are not provided in the operation portion 4 as they are in the present embodiment will be described.

Figure 7:
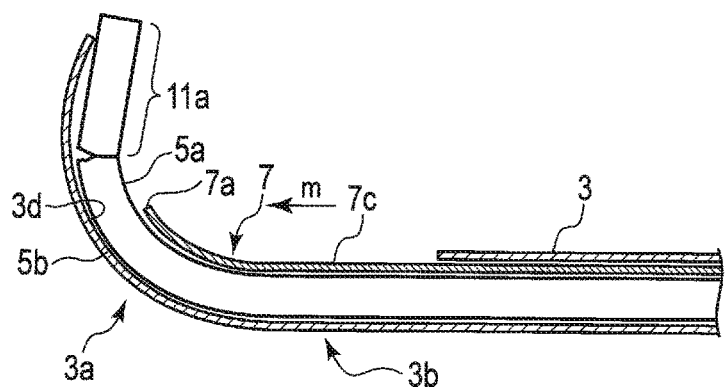
FIG. 7 is a diagram showing a state in which an abnormality has occurred in accordance with the shape of the angle adjustment portion due to movement of only the movable guide at the distal end portion of the insertion assist system.

It is assumed that, after the insertion into the body cavity, the guide operation portion S2 is moved in a state in which the distal end portion 11a of the insertion body 11 is in contact with the distal end 3c of the angle adjustment portion 3a. That is, as shown in FIG. 7, only the movable guide 7 moves so as to slide on the insertion body 11, and the guide distal end portion 7a presses the inside bend 5a of the peripheral surface of the insertion body 11 against the curved guide surface 3d of the angle adjustment portion 3a. When the guide surface (bending portion) 3d of the angle adjustment portion 3a is recessed like a concave surface, a load may be applied to the boundary between the linear distal end portion 11a made of a rigid member and the flexible member following the rear end of the rigid member in the insertion body 11. Although the degree of this load depends on the bending angle of the angle adjustment portion 3a with respect to the linear portion 3b, it is not preferable that the load be applied to the peripheral surface of the insertion body 11 in the cross-sectional direction of the insertion body 11.

On the other hand, according to the configuration of the operation portion 4 of the present embodiment shown in FIG. 4A, as shown in FIG. 5, the guide operation element 26 is moved and operated in a state in which the distal end portion 11a of the insertion body 11 remains in contact with the distal end 3c of the angle adjustment portion 3a. At this time, the locking member 25 provided integrally with the guide operation element 26 moves; however, since the insertion body 11 passes through the through hole 25a, the insertion body 11 does not move and maintains the current position. Through this movement, the locking member 25 comes into contact with a certain position of the stopper portion 22a of the gripping member 22. After coming into contact with the stopper portion 22a, the locking member 25 is continuously moved to press the gripping member 22 together with the stopper portion 22a, and integrally presses the insertion body 11 toward the distal end in the m direction.

Figure 6:
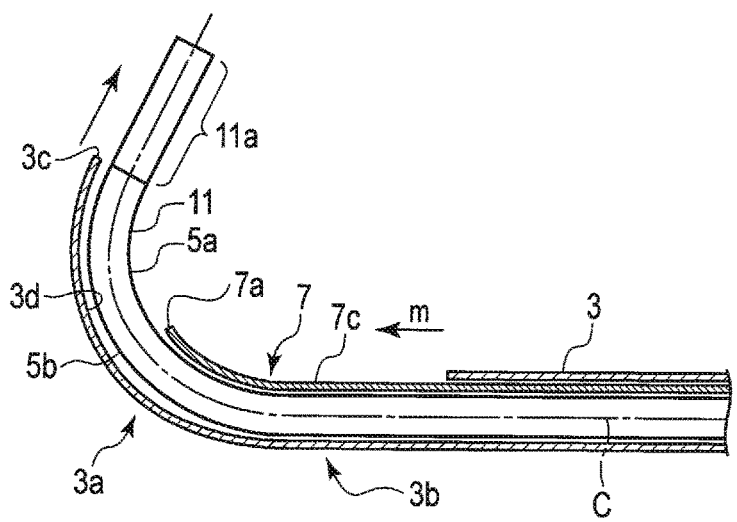
FIG. 6 is a diagram showing a state in which the movable guide at the distal end portion of the insertion assist system is moved together with the insertion body.

As shown in FIG. 6, the distal end portion 11a of the insertion body 11 is pushed out and projects from the distal end 3c of the angle adjustment portion 3a. At the same time as the distal end portion 11a projects from the distal end 3c of the angle adjustment portion 3a, the guide distal end portion 7a of the movable guide 7 abuts against the inside bend 5a of the flexible insertion body 11 following the distal end portion 11a, so that the guide distal end portion 7a pushes the insertion body 11 to the position Ho where the arc is the deepest in the guide surface 3d of the angle adjustment portion 3a, and the outside bend 5b of the insertion body 11 is caused to follow the bending shape of the angle adjustment portion 3a. Therefore, the insertion assist system 2 can prevent the distal end portion 11a of the insertion body 11 from being forcibly pressed against the bent guide surface 3d of the angle adjustment portion 3a as described above, and can prevent the distal end portion 11a from being deformed or a load from being applied to the boundary between the distal end portion 11a and the flexible member.

The operation portion 4 includes the braking member 24 in the housing of the operation portion 4. The braking member 24 is formed of, for example, soft rubber or sponge, into a plate shape. The braking member 24 uses a braking force mainly including a resistance force [amount of force] due to friction generated by the contact between the bottom of the stopper portion 22a and the braking member 24 and between the bottom surface of the locking member 25 and the braking member 24. Due to this braking force, the positions of the movement operation element 21 and the guide operation element 26 are maintained even when fingers are separated from the movement operation element 21 and the guide operation element 26. That is, the braking member 24 prevents the movable guide 7 and the insertion body 11 from moving unintentionally. Since the movable guide 7 and the insertion body 11 maintain their current positions, the observation direction and the projection direction of the distal end portion 11a of the insertion body 11 are maintained.

Further, the braking member 24 is in line contact with the bottom of the stopper portion 22a, and in surface contact with the bottom surface of the locking member 25. Therefore, the braking member 24 requires a larger amount of force to move and a higher braking force must be set for the movable guide 7, as compared to the insertion body 11.

The operation frequency of the movement operation portion S1 to move the insertion body 11 for insertion and removal is higher than the operation frequency of the guide operation portion S2 to move the movable guide 7. For this reason, the amount of operation force (here, difficulty in movement) of the guide operation portion S2 is set greater than that of the movement operation portion S1. Accordingly, even if the operator operates the movement operation element 21 to insert the insertion body 11 at an appropriate position, the movable guide 7 is difficult to move. Therefore, even when the insertion body 11 is moved, the bending state of the insertion body 11 by the angle adjustment portion 3a is maintained, and the operator can insert or remove the insertion body 11 to or from an appropriate position without shifting the observation direction and the protruding direction.

Figure 8:
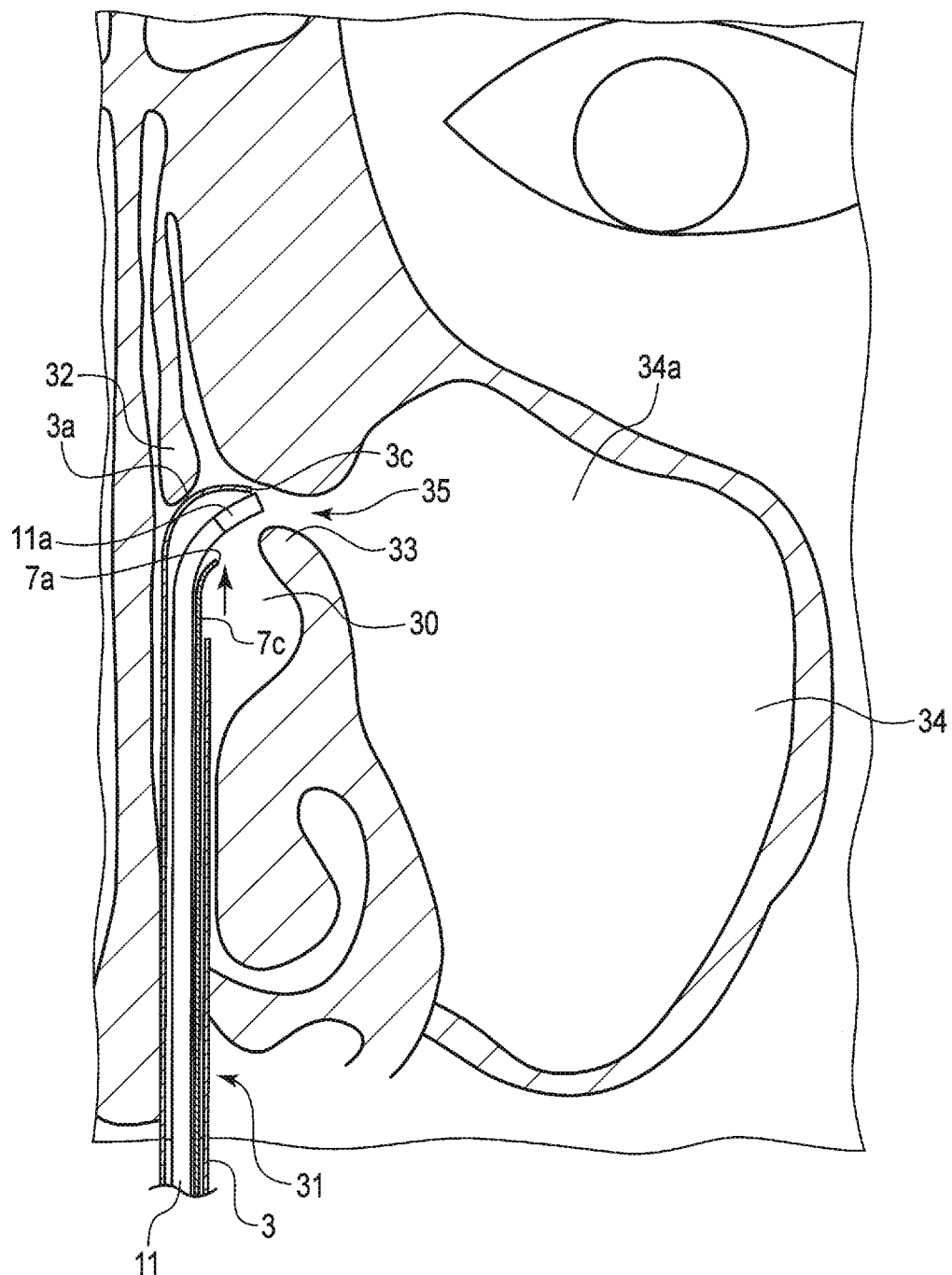
FIG. 8 is a diagram showing a state before insertion of a paranasal sinus endoscope into a maxillary sinus of a paranasal sinus using the insertion assist system.
Figure 9:
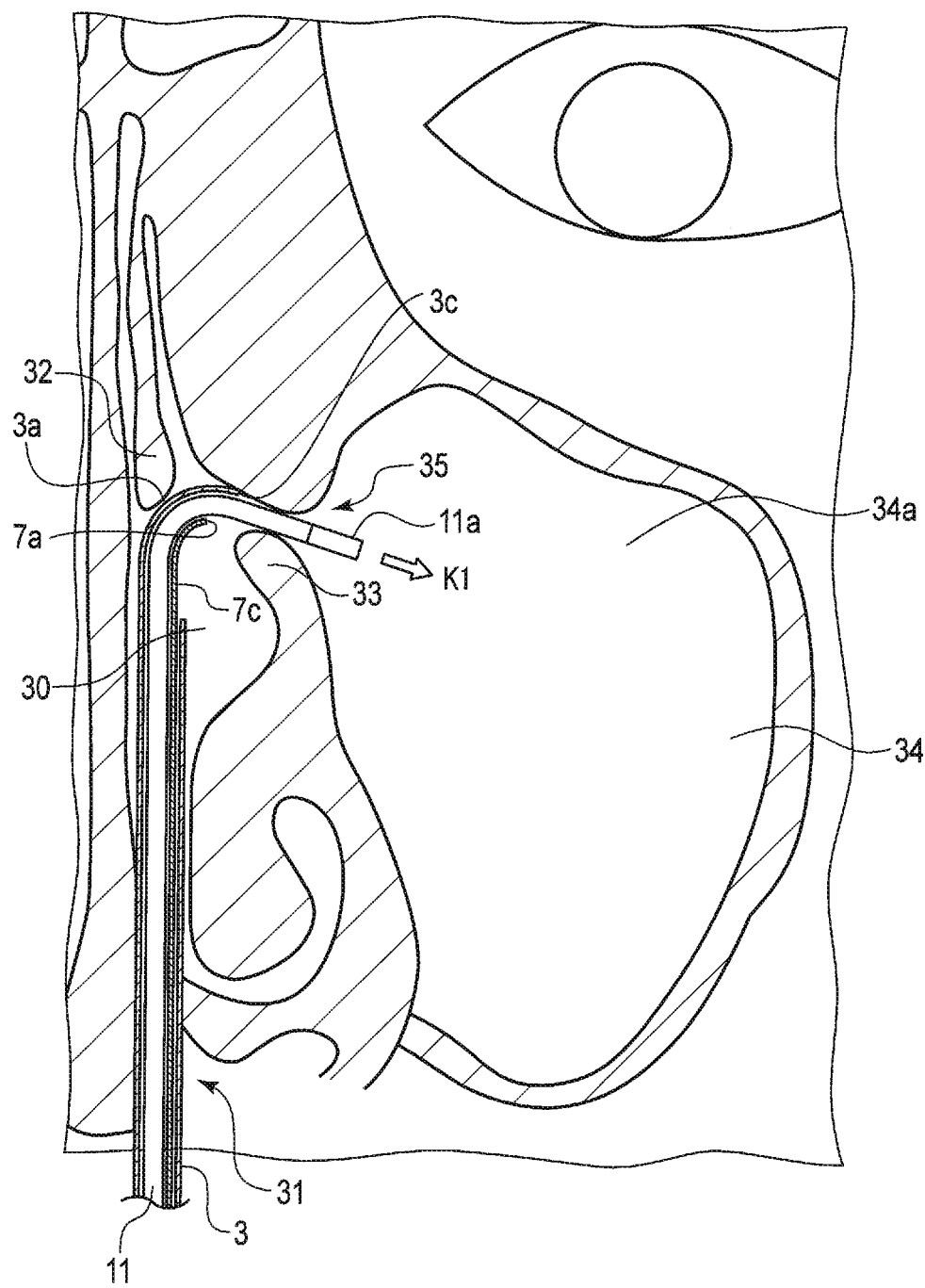
FIG. 9 is a diagram showing a state in which the paranasal sinus endoscope has been inserted into the maxillary sinus of the paranasal sinus using the insertion assist system.
Figure 10:
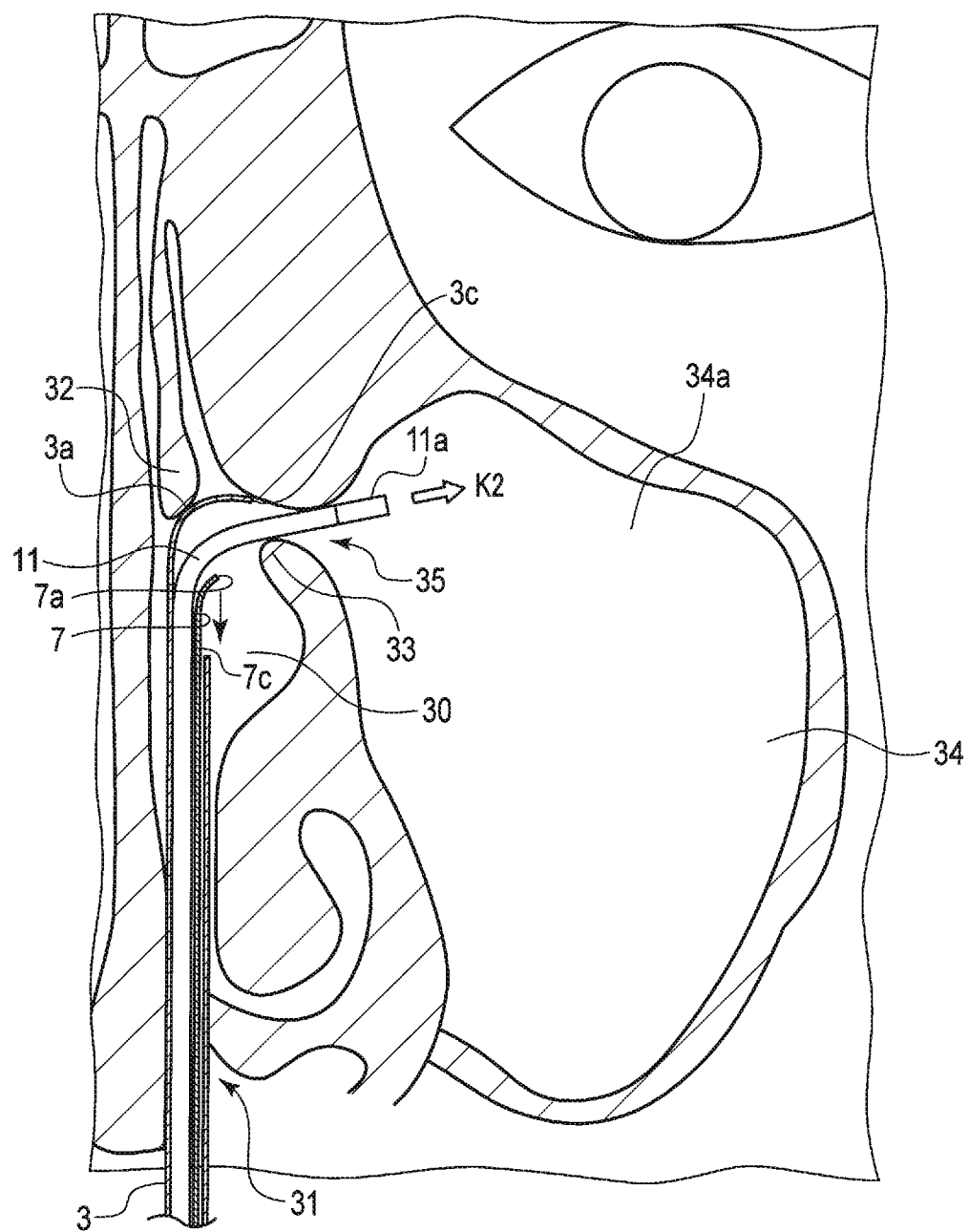
FIG. 10 is a diagram showing a state of adjusting an angle of the paranasal sinus endoscope that has been inserted into the maxillary sinus of the paranasal sinus using the insertion assist system.

Next, a specific example in which the flexible endoscope 1 is applied to a paranasal sinus endoscope to observe a paranasal sinus will be described. FIG. 8 is a diagram showing a state before insertion of the paranasal sinus endoscope into a maxillary sinus of a paranasal sinus using the insertion assist system 2. FIG. 9 is a diagram showing a state in which the paranasal sinus endoscope has been inserted into the maxillary sinus. FIG. 10 is a diagram showing a state of adjusting an angle of the paranasal sinus endoscope that has been inserted into the maxillary sinus.

In the insertion assist system 2 of the present embodiment, first, the guide operation element 26 (see FIG. 4A) is moved backward along the sliding slit 4c of the operation portion 4, so that the movable guide 7 is retracted to the rear end side. In this state, the movement operation element 21 is moved forward along the sliding slit 4b of the operation portion 4, so that the distal end portion 11a of the insertion body 11 of the paranasal sinus endoscope 1 is pushed out to the distal end 3c of the angle adjustment portion 3a of the fixed guide 3.

Next, as shown in FIG. 8, the lumen from a nasal cavity 30 to a paranasal sinus 34 is bent sideways in the middle of the path (to the right in FIG. 8), and is connected to the paranasal sinus 34 via a middle nasal concha 32 and an uncinate process 33. In order to observe the inside of the maxillary sinus 34a of the paranasal sinus 34, the operator inserts the angle adjustment portion 3a of the fixed guide 3 into the nasal cavity 30 from an external naris 31, and causes the distal end 3c of the angle adjustment portion 3a and the distal end portion 11a of the insertion body 11 to reach the vicinity of the opening portion 35 of the maxillary sinus 34a while pushing away the middle nasal concha 32 by the angle adjustment portion 3a.

Next, as described above, the operator operates the guide operation element 26 to move the movable guide 7 to the distal end side of the fixed guide 3. By this operation, as shown in FIG. 9, the distal end portion 11a of the insertion body 11 projects from the distal end 3c of the angle adjustment portion 3a in the direction K1 passing through the opening portion 35.

Since the distal end portion 11a of the insertion body 11 has passed through the opening portion 35, the operator can observe in the direction K1 (inside the maxillary sinus 34a) passing through the opening portion 35 using the endoscope 1. To shift the observation direction toward a target from the direction K1 to the direction K2 (see FIG. 10), the operator pulls the guide operation element 26 toward the rear end of the operation portion 4. By pulling the guide operation element 26 toward the rear end of the operation portion 4, the movable guide 7 returns to the proximal end of the fixed guide 3, and the resilience of the insertion body 11 acts to return the bending shape to a linear shape. Therefore, as shown in FIG. 10, the distal end portion 11a swings from the position shown in FIG. 9 in the direction K2. At this time, the insertion body 11 may swing about the distal end 3c of the angle adjustment portion 3a as a fulcrum, or may swing about the body cavity as a fulcrum. After observing the observation target in the direction K2, the operator pulls the movement operation element 21 to the rear end side of the operation portion 4. The distal end portion 11a of the insertion body 11 is withdrawn from the maxillary sinus 34a and is accommodated in the fixed guide 3. When the observation is completed, the operator removes the fixed guide 3 from the external naris 31.

As described above, the flexible insertion body 11 assisted by the insertion assist system 2 of the present embodiment is inserted into the body cavity of the observation subject person together with the insertion assist system 2, and thereafter the movable guide 7 is moved to pass the insertion body 11 through the opening portion 35 existing on the path leading to the observation target in the body cavity. The guide direction of the distal end portion 11a of the insertion body 11 can be shifted by the movement of the movable guide 7 so that the distal end portion 11a of the insertion body 11 is directed in a discretionary direction. Also, at the time of observation by the flexible endoscope 1 after passing the insertion body 11 through the opening portion 35, the distal end portion 11a of the flexible endoscope 1 can swing, so that a desired observation target inside of the body cavity can be observed by similarly moving the movable guide 7. Therefore, by using the insertion assist system 2 of the present embodiment, the guide direction can be adjusted without removing the distal end portion 11a of the endoscope 1 from the body cavity in order to shift the direction of the distal end portion 11a, so that the time and effort of the operator (observer) can be reduced and the burden of insertion and removal into and from the observation target person can be prevented.

In addition, in the case where the flexible insertion body 11 is the flexible endoscope 1, there is no wasted time involved in insertion into and removal from the observation target person, other than the observation time. Therefore, the total time required for observation can be shortened. In addition, since the cross section of the fixed guide 3 is U-shaped, the flexible insertion body 11 fitted in the fixed guide 3 may not come out of the fixed guide (guide member) 3 during the insertion movement. Therefore, the positional deviation in directions other than the insertion direction can be prevented.

Second Embodiment

Next, with reference to FIG. 11A, FIG. 11B, and FIG. 11C, an insertion assist system 2 applied to a flexible insertion body 42 according to the second embodiment will be described. FIG. 11A is a diagram showing a configuration of a distal end portion of the insertion assist system 2 according to the second embodiment. FIG. 11B is a diagram showing a state of the distal end portion of the insertion assist system 2. FIG. 11C is a cross-sectional view showing a cross-sectional configuration of the distal end portion of the insertion assist system 2 taken along line C-C. With respect to the components of the second embodiment, the same components as those of the above-described first embodiment are denoted by the same reference numerals, and descriptions thereof are omitted.

Normally, the size of the angle adjustment portion 3a, which is the bending portion (guide surface 3d) of the fixed guide 3, that is, the size and length of the bending diameter, varies depending on the observation target. If the insertion body 42 is not bent along the angle adjustment portion 3a which is the bending portion (guide surface 3d) and is separated from the angle adjustment portion 3a, a raised portion will be formed. In such a case, the guide direction cannot be regulated by the angle adjustment portion 3a and the movable guide 7, and the direction of the distal end portion 42a of the flexible insertion body 42 may be different from the direction to be guided.

Therefore, as described above, when the guide distal end portion 7a of the movable guide 7 comes into contact with the side surface (the inside bend 5a) of the insertion body 42 and the outside bend 5b of the flexible insertion body 42 comes into contact with the guide surface 3d of the angle adjustment portion 3a of the fixed guide 3, it is desirable that the insertion body 42 come into contact with the guide surface 3d so as to conform to the shape of the guide surface 3d of the angle adjustment portion 3a. That is, it is preferable that the guide distal end portion 7a of the movable guide 7 have a height H (FIG. 1) that reaches the deepest part of the arc. However, the fixed guide 3 is formed of a single cylindrical tube made of a metal member or a rigid resin member, and has a structure provided with the angle adjustment portion 3a that is bent at the distal end side. Therefore, when the movable guide 7 is inserted from the tube opening on the proximal end side (the side connected to the operation portion 4) of the fixed guide 3, it is easy to insert the movable guide 7, but the height of the guide distal end portion 7a is limited by the tube opening diameter, so that the guide distal end portion 7a may not be as high as desired. On the other hand, since the angle adjustment portion 3a, which is bent, is provided on the distal end side of the fixed guide 3, it is difficult to insert the movable guide 7 from the distal end side of the fixed guide 3, that is, to insert the guide distal end portion 7a from the opening portion of the linear portion 3b.

Therefore, in the present embodiment, as shown in FIG. 11A to FIG. 11C, the fixed guide [first fixed guide] 3 includes a U-shaped linear portion 3b following the angle adjustment portion 3a and a separate cap (cover) [second fixed guide] 41 separated from the linear portion 3b. The cap 41 has a holder portion with support portions 41a on both inner side surfaces. A flat linear portion of the movable guide 7 is accommodated in the holder portion of the cap 41 so as to be slidable (movable forward and backward) with respect to the fixed guide 3. The cap 41 is fixed to the linear portion 3b so as to close the opening of the linear portion excluding the U-shaped linear portion 3b. That is, the cap 41 does not cover the angle adjustment portion (bending portion) 3a of the fixed guide 3 and the range of back-and-forth movement of the guide distal end portion (shift portion) 7a of the movable guide 7. For this reason, the cap 41 closes the opening of the U-shaped linear portion 3b excluding the guide surface 3d of the fixed guide 3 and the range of back-and-forth movement of the distal end portion 7a of the shift member 40.

In FIG. 11A, after the movable guide 7 is inserted into the cap 41, the cap 41 is overlaid on, fitted in and fixed to the U-shaped linear portion 3b from above so as to close the U-shaped opening portion excluding the range of back-and-forth movement of the guide distal end portion 7a. For this fixation, the cap 41 may have a simple fixing structure, such as a snap fit, with respect to the U-shaped linear portion 3b, and the cap 41 may be separable from the fixed guide 3. As shown in FIG. 11B, the cap 41 does not cover the angle adjustment portion (bending portion) 3a of the fixed guide 3 and the range of back-and-forth movement of the guide distal end portion 7a of the movable guide 7. As shown in FIG. 11B, the guide distal end portion 7a of the movable guide 7 has a height that allows the flexible insertion body 42 to be pressed to the deepest part of the guide surface (arc) 3d of the angle adjustment portion 3a.

As described above, since the fixed guide 3 is formed by two constructional elements of the U-shaped linear portion 3b and the cap 41, the size of the guide distal end portion 7a of the movable guide 7 can be selected in accordance with the size and length of the bending diameter of the angle adjustment portion 3a. With this configuration, it is possible to prevent the flexible insertion body 42 from rising from the guide surface 3d of the angle adjustment portion 3a, and to direct the flexible insertion body 42 in the guide direction by the angle adjustment portion 3a. Note that the flexible insertion body 42 applied to the insertion assist system of the present embodiment includes, for example, a flexible endoscope, a catheter, a guide wire, and the like.

Figure 11D:
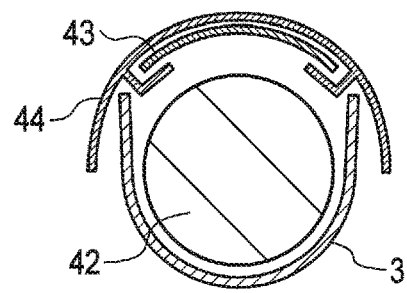
FIG. 11D is a diagram showing a state of the distal end portion of an insertion assist system according to a modification of the second embodiment.

FIG. 11D shows a modification of the second embodiment. In the above-described second embodiment, the linear portion of the movable guide 7 is a flat plate. In this modification, the linear portion of a movable guide 43 is formed, for example, in an arc shape in accordance with the shape of the flexible insertion body 42. The cap 44 and the holder portion that slidably accommodate the movable guide 43 are also formed in an arc shape. According to this modification, since the cross section of the linear portion 3b of the cap 41 of the fixed guide 3 in the second embodiment has an arc shape, the cross-sectional area can be further reduced. For this reason, the outer diameter of the linear portion 3b is reduced. This modification can provide the same function and effects as those of the second embodiment.

Third Embodiment

Figure 12A:
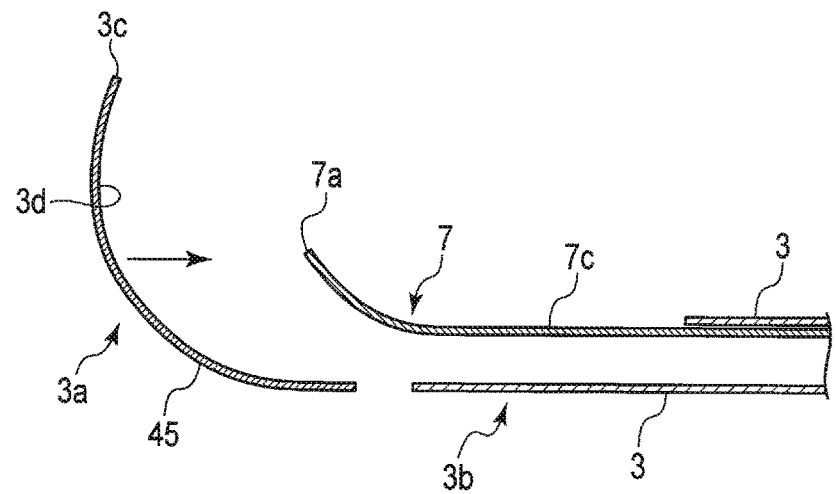
FIG. 12A is a diagram showing a configuration example of a distal end portion of an insertion assist system according to a third embodiment.
Figure 12B:
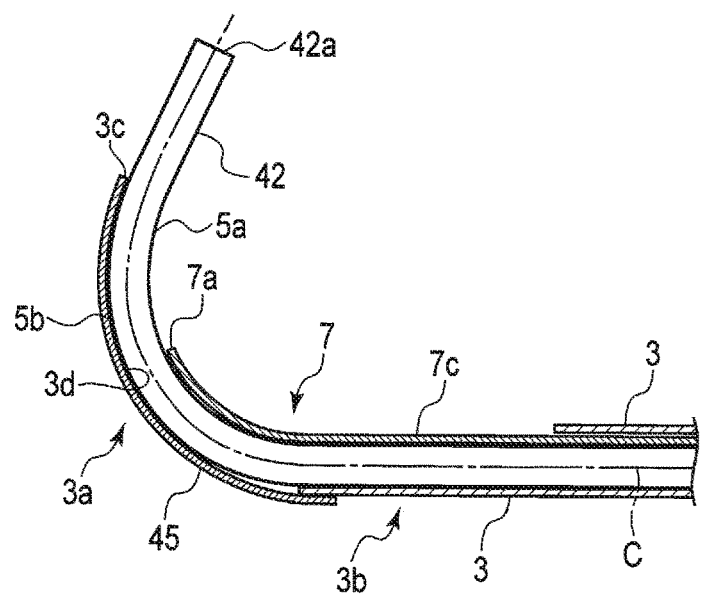
FIG. 12B is a diagram showing a state of the distal end portion of the insertion assist system according to the third embodiment.

Next, an insertion assist system 2 applied to a flexible insertion body 42 according to the third embodiment will be described with reference to FIG. 12A and FIG. 12B. FIG. 12A is a diagram showing a configuration of a distal end portion of the insertion assist system 2 according to the third embodiment. FIG. 12B is a diagram showing a state of the distal end portion of the insertion assist system 2 according to the third embodiment. In the third embodiment, the same components as those in the first and second embodiments are denoted by the same reference numerals, and description thereof will be omitted.

In this embodiment, as in the second embodiment described above, the guide distal end portion 7a having a height (H shown in FIG. 1) is assembled, where the height H allows the flexible insertion body 42 to be brought into contact with the deepest position (for example, Ho shown in FIG. 1) of the arc of the bending guide surface 3d of the angle adjustment portion 3a, which is the bending portion of the fixed guide 3.

In the present embodiment, the fixed guide 3 is configured by an angle adjustment portion 45 and a cylindrical tube including the U-shaped linear portion 3b, which are separate bodies. As shown in FIG. 12A, the linear portion of the movable guide 7 is inserted from the U-shaped linear portion 3b side of the fixed guide 3. Thereafter, the proximal end of the angle adjustment portion 45 having a bending shape equivalent to that of the angle adjustment portion 3a is applied to the distal end of the U-shaped linear portion 3b, and is overlapped and fixed as shown in FIG. 12B. Here, the angle adjustment portion 45 and the fixed guide 3 may be separable. Of course, the connecting surfaces of the angle adjustment portion 45 and the U-shaped linear portion 3b may not necessarily be overlapped, but may be butt-joined together and fixed by welding or the like so that they are on the same surface.

As described above, in the present embodiment, the fixed guide 3 is configured by two constructional elements of the angle adjustment portion 45 and the cylindrical tube including the U-shaped linear portion 3b, whereby the guide distal end portion 7a of the movable guide 7 can be formed and assembled in accordance with the size and length of the bending diameter of the angle adjustment portion 45. With this configuration, similarly to the second embodiment, the flexible insertion body 42 is prevented from rising up from the guide surface 3d of the angle adjustment portion 45, and the distal end portion 42a of the flexible insertion body 42 can be directed in the guide direction determined by the angle adjustment portion 45. Note that the flexible insertion body 42 applied to the insertion assist system 2 of the present embodiment includes, for example, a flexible endoscope, a catheter, a guide wire, and the like.

Fourth Embodiment

Figure 13A:
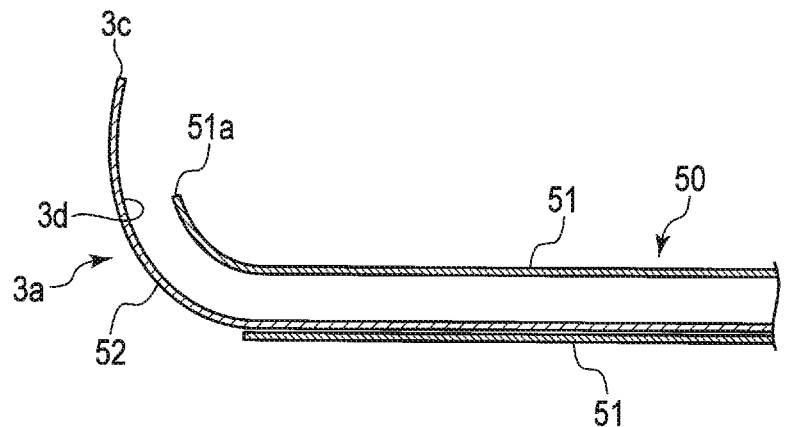
FIG. 13A is a diagram showing a configuration example of a distal end portion of an insertion assist system according to a fourth embodiment.
Figure 13B:
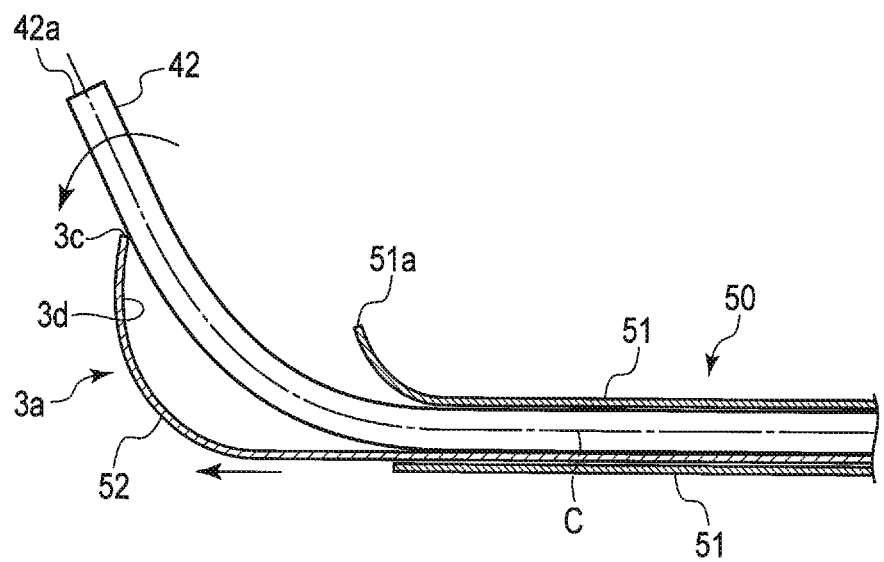
FIG. 13B is a diagram showing a state of the distal end portion of the insertion assist system according to the fourth embodiment.

Next, an insertion assist system 2 applied to a flexible insertion body 42 according to the fourth embodiment will be described with reference to FIG. 13A and FIG. 13B. FIG. 13A is a diagram showing a configuration of a distal end portion of the insertion assist system 2 according to the fourth embodiment. FIG. 13B is a diagram showing a state of the distal end portion of the insertion assist system 2 according to the fourth embodiment. In the fourth embodiment, the same components as those in the first embodiment are denoted by the same reference numerals, and description thereof will be omitted. The present embodiment has a configuration in which the angle adjustment portion 3a in the above-described second embodiment is formed as a separate slidable movable guide, and the guide distal end portion 7a is fixed to the fixed guide 3.

As shown in FIG. 13A, the insertion assist system 2 has a shift member 50 that is configured to shift the direction of the distal end 42a of the insertion body 42. The shift member 50 includes a fixed guide 51 formed of a cylindrical tube, and a fixed guide distal end portion 51a provided at an opening end of the fixed guide 51, having the same shape as the guide distal end portion 7a, and functioning as a pressing member. Furthermore, the proximal end side of a movable guide 52 provided with the angle adjustment portion 3a is inserted from the opening end of the fixed guide 51, and is connected to the guide operation portion S2 of the operation portion 4 (see FIG. 4A). The cross-sectional shape of the movable guide 52 is, for example, U-shaped. Alternatively, only the angle adjustment portion, which is a bending portion, may have a U shape, and the linear portion may have a bar shape. In this configuration, as shown in FIG. 13B, when the angle adjustment portion 3a is fed forward from the fixed guide 51 by the operation of the guide operation portion S2, the flexible insertion body 42 tends to return from the bending state to a nearly linear state due to resilience, and the distal end portion 42a of the flexible insertion body 42 swings. For this reason, the direction of the insertion body 42 is shifted.

As described above, in this embodiment, the angle adjustment portion 3a is provided at the distal end of the movable guide 52 which is to be inserted, and the fixed guide distal end portion 51a is provided at the distal end of the cylindrical tube. Therefore, the fixed guide distal end portion 51a of the fixed guide 51 can be formed in accordance with the size and length of the bending diameter of the angle adjustment portion 3a. With this configuration, similarly to the second embodiment, the flexible insertion body 42 can be prevented from rising up from the guide surface 3d of the angle adjustment portion 3a, and the flexible insertion body 42 can be directed in the guide direction along the guide surface 3d of the angle adjustment portion 3a. Also in the present embodiment, the flexible insertion body 42 applied to the insertion assist system 2 includes, for example, a flexible endoscope, a catheter, a guide wire, and the like.

Fifth Embodiment

Next, an insertion assist system 2 applied to a flexible insertion body 42 according to the fifth embodiment will be described with reference to FIG. 14A and FIG. 14B. FIG. 14A is a diagram showing a configuration of a distal end portion of the insertion assist system 2 according to the fifth embodiment. FIG. 14B is a diagram showing a state of the distal end portion of the insertion assist system 2 according to the fifth embodiment. In the fifth embodiment, the same components as those in the first embodiment are denoted by the same reference numerals, and description thereof will be omitted. The insertion assist system 2 of the present embodiment includes the fixed guide 3, configured by the angle adjustment portion 3a and the linear portion 3b each having a U-shaped cross section, and also includes a shift member 60 that is configured to shift the direction of the distal end 42a of the insertion body 42. The shift member 60 includes a pulling portion 61 including a wire to which a movable guide 62 formed of an annular ring is connected.

The movable guide 62 has a size that allows at least the flexible insertion body 42 to be fitted therein and to be accommodated in a U-shaped groove of the angle adjustment portion 3a when the outside bend 5b of the flexible insertion body 42 is pulled toward the guide surface 3d. The movable guide 62 may be not only a ring having a circular cross section but also a short cylindrical shape having a short rectangular or elliptic cross section.

Further, the pulling portion (pulling member) 61 is made of, for example, a wire, and has one end connected to the movable guide 62 and the other end connected to the guide operation portion S2. The pulling portion 61 may be formed of not only a wire but also a combination of rigid shafts made of a wire and a resin. Further, the pulling portion 61 is pulled into the U-shaped groove from the back surface side through a hole 63 opened in the angle adjustment portion 3a, and is connected to the movable guide 62.

With this configuration, in the operation portion 4, the pulling portion is pulled by sliding the guide operation portion S2 toward the rear end side, and the outside bend 5b of the flexible insertion body 42 is pulled along the guide surface 3d bending along the angle adjustment portion 3a. Furthermore, in the operation portion 4, by sliding the guide operation portion S2 toward the distal end side, as shown in FIG. 14B, the pulling portion 61 is loosened, and the movable guide 62 is separated from the guide surface 3d of the angle adjustment portion 3a by the resilience acting to return the flexible insertion body 42 to the linear shape. At this time, the flexible insertion body 42 tends to return to a straight line while the outside bend 5b of the flexible insertion body 42 is separated from the guide surface 3d. Therefore, the distal end portion 42a of the flexible insertion body 42 swings from the rear end side (as shown in FIG. 14A, obliquely upward to the rear with respect to the fixed guide 3) to the distal end side (as shown in FIG. 14B, obliquely upward to the front with respect to the fixed guide 3).

As described above, in the insertion assist system 2 of the present embodiment, the configuration to adjust the direction and the angle of the distal end portion 42a of the flexible insertion body 42 can be realized with a simple configuration by the fixed guide 3 including the angle adjustment portion 3a, the movable guide 62 formed of an annular ring, and the wire pulling portion 61. Further, it is easy to obtain the configuration in accordance with the size and length of the bending diameter of the angle adjustment portion 3a. With this configuration, similarly to the second embodiment, the flexible insertion body 42 is prevented from rising up from the guide surface 3d of the angle adjustment portion 3a, and the distal end portion 42a of the flexible insertion body 42 can be directed in the guide direction determined by the angle adjustment portion 3a. Also in the present embodiment, the flexible insertion body 42 applied to the insertion assist system 2 includes, for example, a flexible endoscope, a catheter, a guide wire, and the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An insertion assist system comprising:
a guide member that includes a guide surface configured to guide insertion of an insertion body, the guide member being configured to bring an outside bend of a peripheral surface of the insertion body into contact with the guide surface when the insertion body is bent toward the guide surface; and a shift member configured to shift a direction of a distal end of the insertion body, wherein:

the shift member being configured to come into contact with an inside bend of the peripheral surface of the insertion body, as a point of force, opposite to the outside bend of the peripheral surface across a center axis of the insertion body, at a position closer to a proximal end side of the insertion body than a position of the guide surface where the outside bend of the peripheral surface of the insertion body is capable of coming into contact when the insertion body is bent; and the shift member being configured to bend the insertion body toward the guide surface about the guide surface as a fulcrum when the shift member comes into contact with the inside bend and bends the insertion body.

2. The insertion assist system according to claim 1, wherein the guide surface of the guide member is bent in one direction.

3. The insertion assist system according to claim 1, wherein the shift member is configured to move forward and backward with respect to the guide member.

4. The insertion assist system according to claim 3, further comprising an operation portion connected to the shift member, and configured to move the shift member along the guide member, place the insertion body along the guide surface, and set the direction of the distal end of the insertion body.

5. The insertion assist system according to claim 1, wherein:

the guide surface of the guide member is bent in one direction; and the shift member is configured to be brought into contact with the inside bend of the peripheral surface of the insertion body, thereby shifting an angle at which the distal end of the insertion body projects from the distal end of the guide member about the distal end of the guide member as the fulcrum in a state in which the distal end of the insertion body projects distally from a distal end of the guide surface.

6. The insertion assist system according to claim 1, further comprising:

a first operation portion including a gripping member configured to grip the insertion body, and a stopper portion that is provided integrally with the gripping member, the first operation portion being configured to move the gripping member; and a second operation portion that is connected to the shift member, that includes a locking member configured to move the shift member together with the stopper portion after being brought into contact with the stopper portion, and that is configured to project the distal end of the insertion body out of a distal end of the guide surface before a distal end of the shift member is brought into contact with the insertion body.

7. The insertion assist system according to claim 6, wherein:

the insertion body is a flexible endoscope including a rigid portion at the distal end; and the second operation portion is configured to prevent the shift member from being pressed onto the rigid portion of the flexible endoscope.

8. The insertion assist system according to claim 6, comprising a braking member configured to brake the stopper portion and the locking member, wherein the braking member is configured such that a force to move the first operation portion, which removes the insertion body, is greater in amount than a force to move the second operation portion, which places the shift member along the guide surface.

9. The insertion assist system according to claim 1, wherein:

the guide surface of the guide member is bent in one direction;

the guide member is a half pipe having a U-shaped distal end at least including the guide surface; and the shift member is configured to move relative to the guide member and includes a distal end portion of a bending shape corresponding to a bending state of the guide surface.

10. The insertion assist system according to claim 1, wherein the guide member is configured to move relative to the shift member, the guide member including:

a first fixed guide having the guide surface and a linear portion, the guide surface being U-shaped; and a second fixed guide that is provided to close a U-shaped opening portion excluding the guide surface of the first fixed guide and a range of back-and-forth movement of the shift member, and that includes a holder portion configured to slidably accommodate the shift member.

11. The insertion assist system according to claim 1, wherein the guide member is configured to move relative to the shift member, the guide member including:

a first fixed guide having the guide surface; and a second fixed guide having a distal end fixed to a proximal end of the first fixed guide, the second fixed guide comprising a linear portion and configured to accommodate the shift member so as to be movable forward and backward.

12. The insertion assist system according to claim 1, wherein the insertion body includes a flexible endoscope including a paranasal sinus endoscope, a catheter, and a guide wire.

13. The insertion assist system according to claim 1, wherein:

the guide surface of the guide member is bent in one direction; and a distal end of the shift member is configured to move relative to the guide member, and to bend toward a distal end of the guide surface so that the distal end is parallel to the guide surface along a bend of the guide surface.

14. An insertion assist system comprising:

a fixed guide comprising a guide surface extending in a longitudinal direction, the fixed guide having an opening in a radial direction relative to the longitudinal direction, a first distal end of the fixed guide being curved relative to the longitudinal direction; and a movable guide extending in the longitudinal direction and being movable longitudinally in the opening relative to the fixed guide, the movable guide having a second distal end, the second distal end being curved relative to the longitudinal direction;

wherein the second distal end, when the movable guide is moved distally, is configured to contact with an inside bend of a peripheral surface of a flexible insertion body disposed at the first distal end to push an outside bend of the peripheral surface of the flexible insertion body to contact the guide surface at the first distal end.

15. The insertion assist system according to claim 14, wherein a cross section of the first distal end and the second distal end is curved.

\* \* \* \* \*